United States Patent [19]

Atkins

[11] Patent Number: 5,616,815
[45] Date of Patent: Apr. 1, 1997

[54] OLEFIN HYDRATION PROCESS

[75] Inventor: Martin P. Atkins, Ashford, England

[73] Assignee: BP Chemicals Limited, London, England

[21] Appl. No.: 556,646

[22] Filed: Nov. 13, 1995

[30] Foreign Application Priority Data

Nov. 23, 1994 [GB] United Kingdom ............... 9423646

[51] Int. Cl.$^6$ ................................................ C07C 29/04
[52] U.S. Cl. .................................................... 568/700
[58] Field of Search .................................... 568/700

[56] References Cited

U.S. PATENT DOCUMENTS

| | | | |
|---|---|---|---|
| 2,173,187 | 9/1939 | Tanner | 260/641 |
| 2,608,534 | 8/1952 | Fleck | 252/435 |
| 4,212,990 | 7/1980 | Yasahara et al. | 560/241 |
| 4,769,355 | 9/1988 | Glaeser et al. | 502/209 |

FOREIGN PATENT DOCUMENTS

| | | |
|---|---|---|
| 0173189 | 3/1986 | European Pat. Off. . |
| 0352023 | 1/1990 | European Pat. Off. . |
| 4102328 | 7/1992 | Germany . |
| 57-130935 | 8/1982 | Japan . |
| 487384 | 6/1938 | United Kingdom . |

*Primary Examiner*—Joseph Conrad
*Attorney, Agent, or Firm*—Brooks Haidt Haffner & Delahunty

[57] ABSTRACT

This invention relates to a process for hydrating olefins to the corresponding alcohols in the vapour phase in the presence of a catalyst system comprising a heteropolyacid catalyst supported on niobia. By using niobia as support, it is possible not only to increase the space-time-yield of the process but also to prolong the life of the support thereby reducing the frequency with which the support is changed or replaced on a plant. The process is particularly suited to producing ethanol from ethylene and isopropanol from propylene.

19 Claims, No Drawings

OLEFIN HYDRATION PROCESS

The present invention relates to a novel catalyst composition comprising a heteropolyacid supported on niobia and the use as a catalyst thereof in a process for the hydration of olefins to alcohols.

Hydration of olefins such as ethylene or propylene to the corresponding alcohols by hydration thereof in the vapour phase using a phosphoric acid catalyst deposited on a siliceous support is well known. Numerous prior art publications described such a procedure including those disclosed in GB-A-1570650, U.S. Pat. No. 4,808,559, GB-A-1371905, U.S. Pat. No. 4,038,211, U.S. Pat. No. 4,012,452, GB-A-1476534, GB-A-1306141, U.S. Pat. No. 3,996,338 and CAN-A-844004. In each of these prior publications, the nature of the siliceous support used is defined by various parameters including the pore volume, the surface area, the crush strength and the purity of the support. However, none of these documents identify the precise combination of the support and a heteropolyacid catalyst for this purpose.

Some of the prior art publications such as eg GB-A-1281120 describe a liquid phase process for the hydration of olefins using a heteropolyacid catalyst. Furthermore, U.S. Pat. No. 2,173,187 describes a process for the hydration of olefins in the vapour phase to the corresponding alcohols by using as catalyst heteropolyacid, the complex anion of which includes one element from group VI, sub-group A of the Periodic table. It is stated in this reference that the catalyst can be used with or without a support. The supports, when used, are said to be preferably silica gel although other siliceous supports such as silicic acid, Japanese acid clay, bentonite, kieselguhr, or asbestos are also listed. Similarly, JA-A-57130935 describes a process for olefin hydration using a heteropolyacid catalyst supported on activated carbon. Furthermore, U.S. Pat. No. 2,608,534 describes a heteropolyacid supported on a major amount of an inorganic metal oxide or hydroxide as catalyst for a number of general organic reactions including inter alia the hydration of olefins. Amongst the supports disclosed in this publication are alumina, magnesia, thoria, titania and the like and alumina is said to be preferred. However, there is no disclosure of any catalyst or specific process for the hydration of olefins to the corresponding alcohols.

It has now been found that heteropolyacids supported on niobia is a novel catalyst which improves the performance of the heteropolyacid catalyst system.

Accordingly, the present invention is a catalyst composition comprising a heteropolyacid supported on niobia.

The niobia support suitably has an average surface area of at least 100 m$^2$/g, preferably greater than 150 m$^2$/g. Also, the niobia must have an average crush strength of at least 2 Kg force, suitably at least 5 Kg force, preferably at least 6 Kg and more preferably at least 7 Kg. The crush strengths quoted are based on average of that determined for each set of 50 beads/globules on a CHATTILLON tester which measures the minimum force necessary to crush a particle between parallel plates. The bulk density of the support is suitably at least 380 g/l, preferably at least 440 g/l. The niobia support suitably has an average particle diameter of 2 to 10 mm, preferably 4 to 6 mm. The niobia support suitably has an average pore volume in the range from 0.1–1.2 ml/g, preferably from 0.3–1.0 ml/g. The niobia support suitably has an average pore radius (prior to use) of 10 to 1000 Angstroms, preferably an average pore radius of 30 to 500 Angstroms.

Examples of this type of support include niobium oxide hydrate ($Nb_2O_5.nH_2O$, supplied by CBMM, Araxá, Brazil). The niobia support used may be in any shape or form but is suitably in the form of pellets, extrudates, granules, beads or is globular in shape before impregnation thereof with the heteropolyacid.

In order to achieve optimum performance, the niobia support is suitably free of extraneous metals or elements which might adversely affect the catalytic activity of the system. The niobia support suitably has at least 80% w/w purity with respect to the niobia content thereof, ie the impurities which may adversely affect the catalytic activity of the system are less than 20% w/w, preferably less than 10% w/w and more preferably less than 5% w/w.

The term "heteropolyacids" as used herein and throughout the specification is meant to include the free acids and salts thereof. The heteropolyacids used to prepare the olefin hydration catalysts of the present invention therefore include the free acids and the coordination-type salts thereof in which the anion is a complex, high molecular weight entity. Typically, the anion is comprises 2–18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I–VIII in the Periodic Table of elements. These include, for instance, lithium ions; cuptic ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well known anions are named after the original researchers in this field and are known eg as Keggin, Wells-Dawson and Anderson-Evans-Perloff structures.

Heteropolyacids usually have a high molecular weight eg in the range from 700–8500 and include dimeric complexes. They have a relatively high solubility in polar solvents such as water or other oxygenated solvents, especially if they are free acids and in the case of several salts, and their solubility can be controlled by choosing the appropriate counterions. Specific examples of heteropolyacids that may be used as the catalysts in the present invention include:

| | |
|---|---|
| 1-12-tungstophosphoric acid | $H_3[PW_{12}O_{40}].xH_2O$ |
| 1-12-molybdophosphoric acid | $H_3[PMo_{12}O_{40}].xH_2O$ |
| 1-12-tungstosilicic acid | $H_4[SiW_{12}O_{40}].xH_2O$ |
| 1-12-molybdosilicic acid | $H_4[SiMo_{12}O_{40}].xH_2O$ |
| Potassium tungstophosphate | $K_6[P_2W_{18}O_{62}].xH_2O$ |
| Sodium molybdophosphate | $Na_3[PMo_{12}O_{40}].xH_2O$ |
| Ammonium molybdodiphosphate | $(NH_4)_6[P_2Mo_{18}O_{62}].xH_2O$ |
| Sodium tungstonickelate | $Na_4[NiW_6O_{24}H_6].xH_2O$ |
| Ammonium molybdodicobaltate | $(NH_4)[Co_2Mo_{10}O_{36}].xH_2O$ |
| Cesium hydrogen tungstosilicate | $Cs_3H[SiW_{12}O_{40}].xH_2O$ |
| Potassium molybdodivanado phosphate | $K_5[PMoV_2O_{40}].xH_2O$ |
| Copper hydrogen tungstosilicate | $CuH_2[SiW_{12}O_{40}].xH_2O$ |
| Lithium hydrogen tungstosilicate | $Li_3H[SiW_{12}O_{40}].xH_2O$ |

The niobia support is suitably impregnated with a solution of the heteropolyacid which is prepared in turn by dissolving the heteropolyacid in a solvent such as eg an alcohol or distilled water. The support is then added to the solution so formed. The support is suitably left to soak in the solution of the heteropolyacid for a duration of several hours, with periodic manual stirring, after which time it is suitably filtered using a Buchner funnel in order to remove any excess acid. Other impregnation techniques such as the incipient wetness technique can also be used.

The wet catalyst thus formed is then suitably placed in an oven at elevated temperature for several hours to dry, after which time it is allowed to cool to ambient temperature in a dessicator. The weight of the catalyst on drying, the weight of the niobia support used and the weight of the acid on support was obtained by deducting the latter from the former from which the catalyst loading in g/liter was determined. This catalyst (measured by weight) was then used in the olefin hydration process.

It should be noted that the polyvalent oxidation states of the heteropolyacids as stated previously and as represented in the typical formulae of some specific compounds only apply to the fresh acid before it is impregnated onto the niobia support, and especially before it is subjected to the olefin hydration process conditions. The degree of hydration of the heteropolyacid may affect the acidity of the catalyst and hence its activity. Thus, either or both of these actions of impregnation and olefin hydration process may possibly change the hydration and oxidation state of the metals in the heteropolyacids, ie the actual catalytic species under the process conditions may not retain the hydration/oxidation states of the metals in the heteropolyacids used to impregnate the support. Naturally, therefore, it is to be expected that such hydration and oxidation states may also be different in the spent catalysts after the reaction.

The supported heteropolyacid catalysts may also be further modified by the addition of phosphoric acid or other mineral acids thereto.

According to a further embodiment, the present invention is a process for hydrating olefins to the corresponding alcohols in the vapour phase in the presence of a catalyst system comprising a heteropolyacid catalyst supported on niobia.

The process is suitably carried out using the following reaction conditions:

a. the mole ratio of water to olefin passing through the reactor is suitably in the range from 0.1–3.0, preferably 0.1–1.0 b. the gas hourly space velocity (GHSV) of the water/olefin mixture is suitably from 0.010 to 0.25 g/min/cm$^3$ of the catalyst system, preferably from 0.03–0.10 g/min/cm$^3$ of the catalyst system.

c. the heteropolyacid catalyst concentration is from 5 to 40% w/w based on the total weight of the catalyst system, preferably from 10–30% w/w of the total weight of the catalyst system.

The olefin hydration reaction is carried out at a temperature from 150°–350° C. Within this temperature range, the hydration of ethylene to ethanol is suitably carried out at a temperature in the range from its dew point to 350° C., and preferably from 200°–300° C.; the hydration of propylene to isopropanol is suitably carried out at a temperature in the range from its dew point to 300° C., and is preferably from 150°–250° C.

The olefins to be hydrated are suitably ethylene or propylene and the corresponding alcohols formed are suitably ethanol and isopropanol respectively. These olefins may be used pure or as a mixture of olefins to generate a corresponding mixture of alcohols. Thus mixed hydrocarbon feedstocks emerging from eg a refinery such as from a fluid catalytic cracking process and comprising a mixture of C2 and C3 saturated and unsaturated hydrocarbons can be used for this purpose. The process is carried out in the vapour phase, ie both the olefin and water are in the vapour phase over the catalyst system, apart from a small proportion of each gaseous reactant which dissolves in the catalyst system. The hydration reaction is believed to occur between such dissolved reactants. Ethers corresponding to the olefin are formed as by-products during the reaction.

The hydration reaction is carried out by placing the catalyst system in a reactor, sealing the reactor and then heating the catalyst system to the reaction temperature. The catalyst system is heated to a temperature from 170° to 300° C. depending upon the end product desired. For instance, if the end product is ethanol from ethylene, the catalyst system is suitably heated from 225° to 280° C., preferably from 230°–260° C., more preferably from 235°–245° C. On the other hand, if the end product is iso-propanol from propylene, the catalyst system is suitably heated from 180°–225° C., preferably from 185°–205° C. When the catalyst system has attained the desired temperature a charge of the olefin and water in the vapour state is passed through the reactor. The mole ratio of water to olefin passing through the reactor is suitably in the range from 0.1 to 3.0, preferably from 0.1 to 1.0, more preferably from 0.25–0.45. The space velocity of water vapour/olefin mixture passing through the reactor is subject to slight variations depending upon whether the reactant olefin is ethylene or propylene. For instance, in the case of ethylene, the space velocity of the mixture thereof with water vapour is suitably from 0.010 to 0.100, preferably from 0.020 to 0.050 grammes per minute per cm$^3$ of the catalyst system. In the case of a mixture of propylene and water vapour, the space velocity is suitably in the from 0.010–0.100, preferably from 0.02–0.07 g/min/cm$^3$ of the catalyst system.

The hydration reaction is carried out at a pressure ranging from 1000–25000 KPa. Within this range, the hydration of ethylene is suitably carried out at a pressure from 3000 to 10000 KPa, whereas the hydration of propylene is suitably carried out at a pressure from 2000–7600 KPa.

The activity of the catalyst system was measured by monitoring the total amount of alcohol, ether and unreacted olefin produced over a one-hour period at standard test conditions (specified in the Examples below).

Alcohol and ether production was measured by gas chromatography (see below), whereas unreacted olefin was metered using a wet-type positive displacement flow meter.

Thus, it has now been found that by using the specific niobia support described herein it is possible not only to increase the space-time-yield (hereafter "STY") of the process but also to prolong the life of the support thereby reducing the frequency with which the support is changed or replaced on a plant.

The present invention is further illustrated with reference to the following Examples:

EXAMPLE 1

Description of the General Procedure & Equipment used

The supported catalyst (20 ml) was charged to a microreactor. The pressure was increased to 6800 KPa in the inert gas, nitrogen (413 ml/min), and the temperature raised to 260° C. (at the rate of 1° C. per minute). The mass of the catalyst used in the Example is shown below. When the temperature was stable at 260° C., water was introduced (at the rate of 0.11 ml/min as liquid) whilst maintaining the inert gas (nitrogen) flow. The water/nitrogen flow were maintained for 30 minutes. The nitrogen flow was stopped and ethylene was introduced at a gas hourly space velocity (GHSV) of about 1240 per hour. The water/ethylene ratio was 0.3 molar. The catalyst activity was monitored (see Table 1 below for results). This was achieved by collecting product over 2-3 hours and analysing the gas and liquid feeds by GC. The catalysts were evaluated at 260° C. and 240° C.

In this Example, the hydration of ethylene was carried out using a silicotungstic acid catalyst supported on niobium oxide. The supported catalyst was prepared by dissolving silicotungstic acid [$H_4SiW_{12}O_{40}$] (18.18 g) in distilled water (50 ml). The solution was mixed with crushed niobium oxide (33.74 g) prepared by tabletting a fine powder of niobium oxide hydrate ($Nb_2O_5.nH_2O$, supplied by CBMM, Araxá, Brazil) using 10 tonnes force and the resultant tablets were crushed to a particle size of 1.0–1.4 mm. The mixture of niobium oxide support and the acid solution was allowed to stand for 24 hours with intermittent stirring. Excess acid was removed from the supported catalyst by filtration. The filtered, supported catalyst was then dried overnight at 120° C. The mass of the supported catalyst after drying was 34.88 g.

The aim of this Example was to test under standard conditions (GHSV of ethylene=1240/hr, water to ethylene mole ratio=0.3, temperature=260° C. and pressure=6800 KPa) and then to observe the effect of reducing the applied temperature. The water flow was set at 0.33 molar with respect to ethylene. The supported catalyst volume used was 20 cm$^3$ and the mass of the supported catalyst used was 24.6 g. The pellet sizes of the supported catalyst used ranged from 1.0–1.4 mm. The GHSV was calculated at standard temperature and pressure. The reaction conditions used and the results achieved are shown in Table 1 below:

TABLE 1

| HOS | TEMP (°C.) | PRESS (KPa) | $H_2O:C_2H_4$ mol ratio | GHSV $C_2H_4$ | g/Liter cat/hr $C_2H_4$ | g/Liter cat/hr $H_2O$ | Conversion Mol % $C_2H_4$ | Conversion Mol % $H_2O$ | Sely* C2 Mol % EtOH | Sely* C2 Mol % DEE | STY (g/l cat/h) EtOH | STY (g/l cat/h) DEE |
|---|---|---|---|---|---|---|---|---|---|---|---|---|
| 4  | 260 | 6800 | 0.38 | 1095 | 1368 | 330 | 2.0 | 4.9 | 83  | 17 | 38 | 6  |
| 6  | 260 | 6800 | 0.33 | 1228 | 1535 | 330 | 3.1 | 8.2 | 76  | 24 | 60 | 15 |
| 10 | 260 | 6800 | 0.36 | 1141 | 1426 | 330 | 2.5 | 6.6 | 89  | 11 | 52 | 5  |
| 12 | 260 | 6800 | 0.35 | 1181 | 1476 | 330 | 2.7 | 7.4 | 90  | 10 | 59 | 6  |
| 14 | 260 | 6800 | 0.34 | 1210 | 1513 | 330 | 2.5 | 7.0 | 90  | 10 | 56 | 5  |
| 18 | 240 | 6800 | 0.35 | 1182 | 1478 | 330 | 1.0 | 2.9 | 100 | 0  | 24 | 0  |
| 20 | 240 | 6800 | 0.33 | 1245 | 1556 | 330 | 0.9 | 2.6 | 95  | 5  | 22 | 1  |
| 22 | 240 | 6800 | 0.33 | 1236 | 1545 | 330 | 0.9 | 2.6 | 98  | 2  | 22 | 0  |

*Selectivity

I claim:

1. A process for the hydration of olefins to the corresponding alcohols in the vapour phase in the presence of a catalyst system comprising a heteropolyacid catalyst supported on niobia.

2. A process according to claim 1 wherein the supported heteropolyacid catalyst used for the olefin hydration reaction is further modified by the addition of phosphoric acid or other mineral acids thereto.

3. A process according to claim 1 wherein the hydration reaction is carried out at a pressure ranging from 1000–25000 KPa.

4. A process according to claim 1 wherein the olefin to be hydrated is a pure olefin or a mixture of olefins resulting in a corresponding mixture of alcohols.

5. A process according to claim 1 wherein the olefin reactant is sourced from a mixed hydrocarbon feedstock emerging from a refinery and comprises a mixture of C2 and C3 saturated and unsaturated hydrocarbons.

6. A process according to claim 1 wherein the olefin hydration reaction is carried out at a temperature from 150°–350° C.

7. A process according to claim 1 wherein ethylene is hydrated to ethanol at a temperature in the range from the dew point of the feed gases to 350° C.

8. A process according to claim 7 wherein said hydration reaction is carried out at a temperature in the range from 200°–300° C.

9. A process according to claim 7 wherein the space velocity of the mixture thereof with water vapour is suitably from 0.020 to 0.050 grammes per minute per cm$^3$ of the catalyst system.

10. A process according to claim 1 wherein propylene is hydrated to isopropanol at a temperature in the range from the dew point of the feed gases to 300° C.

11. A process according to claim 10 wherein the hydration reaction is carried out at a temperature from 150°–250° C.

12. A process according to claim 10 wherein the space velocity of the mixture thereof with water vapour is suitably from 0.020 to 0.070 grams per minute per cm$^3$ of the catalyst system.

13. A process according to claim 1 wherein the niobia support has a surface area greater than 100 m$^2$/g.

14. A process according to claim 1 wherein the niobia support is shaped into the form of pellets or beads or globular shape by pelletisation or extrusion.

15. A process according to claim 1 wherein the niobia support has an average particle diameter of 2 to 10 mm, an average pore volume in the range from 0.3–1.2 ml/g, an average pore radius (prior to use) of 10 to 1000 angstroms, a bulk density of at least 380 g/l and an average crush strength of at least 2 Kg force.

16. A process according to claim 1 wherein the niobia support is free of extraneous metals or elements and has at least 80% w/w purity with respect to the aluminosilicate content thereof.

17. A process according to claim 1 wherein the heteropolyacids catalysts used are selected from the free heteropolyacids and the coordination-type salts thereof comprising a central atom complexed with an anion in which the anion is a complex, high molecular weight entity and comprises 2–18 oxygen-linked polyvalent metal peripheral atoms surrounding a central atom or ion from Groups I–VIII of the Periodic Table of Elements.

18. A process according to claim 1 wherein the polyvalent metal peripheral atom is one of more of molybdenum, tungsten, vanadium, niobium and tantalum, and the central atom or ion is selected from lithium ions; cupric ions; divalent beryllium, zinc, cobalt or nickel ions; trivalent boron, aluminum, gallium, iron, cerium, arsenic, antimony, phosphorus, bismut, chromium or rhodium, ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions.

19. A process according to claim 1 wherein the heteropolyacid catalyst is selected from the group consisting of:

| | |
|---|---|
| 1–12-tungstophosphoric acid | $H_3[PW_{12}O_{40}].xH_2O$ |
| 1–12-molybdophosphoric acid | $H_3[PMo_{12}O_{40}].xH_2O$ |
| 1–12-tungstosilicic acid | $H_4[SiW_{12}O_{40}].xH_2O$ |
| 1–12-molybdosdicic acid | $H_4[SiMo_{12}O_{40}].xH_2O$ |
| Potassium tungstophosphate | $K_6[P_2W_{18}O_{62}].xH_2O$ |
| Sodium molybdophosphate | $Na_3[PMo_{12}O_{40}].xH_2O$ |
| Ammonium molybdodiphosphate | $(NH_4)_6[P_2Mo_{18}O_{62}].xH_2O$ |
| Sodium tungstonickelate | $Na_4[NiW_6O_{24}H_6].xH_2O$ |
| Ammonium molybdodicobaltate | $(NH_4)[Co_2Mo_{10}O_{36}].xH_2O$ |
| Cesium hydrogen tungstosilicate | $Cs_3H[SiW_{12}O_{40}].xH_2O$ |
| Potassium molybdodivanado phosphate | $K_5[PMoV_2O_{40}].xH_2O$ |
| Copper hydrogen tungstosdicate | $CuH_2[SiW_{12}O_{40}].xH_2O$ |
| Lithium hydrogen tungstosdicate | $Li_3H[SiW_{12}O_{40}].xH_2O$ |

\* \* \* \* \*

UNITED STATES PATENT AND TRADEMARK OFFICE
CERTIFICATE OF CORRECTION

PATENT NO. : 5,616,815
DATED : April 1, 1997
INVENTOR(S) : MARTIN P. ATKINS

It is certified that error appears in the above-indentified patent and that said Letters Patent is hereby corrected as shown below:

Col. 2, 1. 31, correct the spelling of the word "cupric"

Claim 19, line 5, col. 8, correct the spelling of the word "molybdosilicic"

Claim 19, line 14, col. 8, correct the spelling of the word "tungstosilicate"

Claim 19, line 15, col. 8, correct the spelling of the word "tungstosilicate"

Signed and Sealed this

Twenty-third Day of September, 1997

Attest:

BRUCE LEHMAN

Attesting Officer

Commissioner of Patents and Trademarks